United States Patent
Mecklenburg et al.

(10) Patent No.: US 11,304,829 B2
(45) Date of Patent: Apr. 19, 2022

(54) ELECTROMAGNETIC LOCKING ELEMENT FOR A JOINT ORTHOSIS OR A JOINT PROSTHESIS

(71) Applicant: Ottobock SE & Co. KGaA, Duderstadt (DE)

(72) Inventors: Arno Mecklenburg, Berlin (DE); Erik Albrecht-Laatsch, Rosdorf (DE); Michael Nolte, Seeburg (DE); André Müller, Duderstadt (DE)

(73) Assignee: OTTOBOCK SE & CO KGAA, Duderstadt (DE)

( * ) Notice: Subject to any disclaimer, the term of this patent is extended or adjusted under 35 U.S.C. 154(b) by 72 days.

(21) Appl. No.: 16/482,944

(22) PCT Filed: Jan. 31, 2018

(86) PCT No.: PCT/EP2018/052349
§ 371 (c)(1),
(2) Date: Aug. 1, 2019

(87) PCT Pub. No.: WO2018/141770
PCT Pub. Date: Aug. 9, 2018

(65) Prior Publication Data
US 2020/0008960 A1    Jan. 9, 2020

(30) Foreign Application Priority Data
Feb. 1, 2017   (DE) .................. 102017000902.3

(51) Int. Cl.
*A61F 2/70* (2006.01)
*A61F 5/01* (2006.01)
(Continued)

(52) U.S. Cl.
CPC .................. *A61F 2/70* (2013.01); *A61F 2/68* (2013.01); *A61F 5/0125* (2013.01); A61F 2/64 (2013.01);
(Continued)

(58) Field of Classification Search
CPC .. A61F 2/70; A61F 2/68; A61F 5/0125; A61F 2/64; A61F 2002/6854;
(Continued)

(56) References Cited

U.S. PATENT DOCUMENTS

| | | | | | |
|---|---|---|---|---|---|
| 2,535,489 | A | * | 12/1950 | Edwards | A61F 2/58 623/24 |
| 2,662,228 | A | * | 12/1953 | Bennington | A61F 2/64 623/24 |

(Continued)

FOREIGN PATENT DOCUMENTS

| | | |
|---|---|---|
| DE | 10311189 A1 | 10/2001 |
| DE | 10311187 A1 | 10/2004 |

(Continued)

*Primary Examiner* — Yashita Sharma
*Assistant Examiner* — Melissa A Hoban
(74) *Attorney, Agent, or Firm* — Holland & Hart LLP

(57) ABSTRACT

An electromagnetic locking element for locking a joint orthosis or joint prosthesis such as a knee orthosis or knee prosthesis. The electromagnetic locking element includes a bistable solenoid with at least one coil and at least one permanent magnet, a pin, which can be retracted and extended with the aid of the solenoid for locking the joint, one or several electrical energy stores such as capacitors, and an electrical control system, which, with the aid of semiconductor switches, discharges the energy store or stores via the at least one coil of the solenoid in such a way that the pin is extended.

20 Claims, 4 Drawing Sheets

(51) Int. Cl.
*A61F 2/68* (2006.01)
*A61F 2/64* (2006.01)

(52) U.S. Cl.
CPC .............. *A61F 2002/6854* (2013.01); *A61F 2002/6863* (2013.01); *A61F 2002/701* (2013.01); *A61F 2002/704* (2013.01); *A61F 2005/0158* (2013.01); *A61F 2005/0179* (2013.01)

(58) Field of Classification Search
CPC ........ A61F 2002/6863; A61F 2002/701; A61F 2002/704; A61F 2005/0158; A61F 2005/0179
See application file for complete search history.

(56) References Cited

U.S. PATENT DOCUMENTS

| | | | | |
|---|---|---|---|---|
| 2,692,910 | A * | 10/1954 | Pye | G07F 17/40 178/18.03 |
| 3,223,802 | A * | 12/1965 | Horst | H01H 50/20 335/267 |
| 3,259,958 | A * | 7/1966 | Lemelson | B23Q 7/045 408/3 |
| 3,553,738 | A * | 1/1971 | Liberson | A61F 2/70 623/24 |
| 3,557,387 | A * | 1/1971 | Ohlenbusch et al. | A61F 2/58 623/24 |
| 3,683,239 | A * | 8/1972 | Sturman | H01H 50/20 361/194 |
| 3,689,103 | A * | 9/1972 | Meulendyk | B60G 17/04 280/5.513 |
| 3,778,697 | A * | 12/1973 | Link | H01F 7/13 322/3 |
| 4,067,070 | A * | 1/1978 | Seamone | A61F 2/58 623/24 |
| 4,604,098 | A * | 8/1986 | Seamone | A61F 2/582 623/60 |
| 4,636,221 | A * | 1/1987 | Kemp | A61F 2/582 623/59 |
| 4,792,338 | A * | 12/1988 | Rennerfelt | A61F 2/583 623/64 |
| 5,314,500 | A * | 5/1994 | Weddendorf | A61F 2/582 623/57 |
| 5,458,655 | A * | 10/1995 | Bozeman, Jr. | A61B 5/1121 623/24 |
| 5,599,003 | A * | 2/1997 | Seemann | H01F 7/124 251/129.2 |
| 5,954,621 | A * | 9/1999 | Joutras | A63B 21/157 482/114 |
| 6,113,642 | A * | 9/2000 | Petrofsky | F16F 9/46 623/24 |
| 6,165,226 | A | 12/2000 | Wagner | |
| 6,265,956 | B1 * | 7/2001 | Cascolan | H01F 7/1615 335/234 |
| 6,500,138 | B1 * | 12/2002 | Irby | A61F 5/0125 602/26 |
| 6,517,585 | B1 * | 2/2003 | Zahedi | A61F 2/70 623/24 |
| 7,410,471 | B1 * | 8/2008 | Campbell | A61B 5/6829 602/16 |
| 9,913,738 | B1 * | 3/2018 | Fikes | A61F 2/70 |
| 2002/0183673 | A1 * | 12/2002 | Naft | A61F 5/0125 602/16 |
| 2003/0109817 | A1 * | 6/2003 | Berl | A61F 5/0123 602/5 |
| 2004/0163722 | A1 * | 8/2004 | Cornea | F01L 1/34 137/625.69 |
| 2004/0225242 | A1 | 11/2004 | Lidolt et al. | |
| 2005/0039762 | A1 | 2/2005 | Lidolt et al. | |
| 2005/0113652 | A1 * | 5/2005 | Stark | A63B 24/0006 600/300 |
| 2006/0167562 | A1 * | 7/2006 | Williams, III | A61F 2/70 623/24 |
| 2007/0032884 | A1 | 2/2007 | Veatch | |
| 2008/0097269 | A1 * | 4/2008 | Weinberg | A61F 5/0125 602/16 |
| 2010/0082115 | A1 | 4/2010 | Kapelke | |
| 2010/0274365 | A1 * | 10/2010 | Evans | A61F 2/581 623/57 |
| 2010/0286791 | A1 * | 11/2010 | Goldsmith | A61B 17/0057 623/23.7 |
| 2011/0031839 | A1 * | 2/2011 | Fullerton | H01F 13/003 310/152 |
| 2011/0247376 | A1 * | 10/2011 | Umbaugh | B66B 13/16 70/91 |
| 2013/0073941 | A1 * | 3/2013 | Evans | G06F 40/177 715/227 |
| 2013/0253393 | A1 | 9/2013 | Schilling | |
| 2014/0303539 | A1 * | 10/2014 | Baym | A61B 8/0875 602/23 |
| 2015/0062770 | A1 | 3/2015 | Robertson | |
| 2015/0197256 | A1 * | 7/2015 | Chedal Bornu | B61B 12/06 105/149.2 |
| 2016/0296347 | A1 * | 10/2016 | Boender | A61F 2/642 |
| 2016/0376742 | A1 * | 12/2016 | Mcdonald | E05B 47/0004 8/137 |
| 2017/0128312 | A1 * | 5/2017 | Park | F16H 21/06 |
| 2017/0304086 | A1 * | 10/2017 | Kuiken | A61F 2/80 |
| 2019/0374213 | A1 * | 12/2019 | Goldsmith | A61F 2/042 |

FOREIGN PATENT DOCUMENTS

| | | |
|---|---|---|
| DE | 102008027639 A1 | 12/2009 |
| DE | 102008059907 A1 | 6/2010 |
| DE | 102010025766 A1 | 1/2012 |
| DE | 102011108464 A1 | 1/2013 |
| DE | 102012104173 A1 | 11/2013 |

* cited by examiner

ELECTROMAGNETIC LOCKING ELEMENT FOR A JOINT ORTHOSIS OR A JOINT PROSTHESIS

CROSS REFERENCE TO RELATED APPLICATIONS

This application is a U.S. National Entry and claims priority to PCT International Patent Application No. PCT/EP2018/052349, filed 31 Jan. 2018, and entitled "ELECTROMAGNETIC LOCKING ELEMENT FOR A JOINT ORTHOSIS OR A JOINT PROSTHESIS," which claims priority to Germany Patent Application No. 102017000902.3 filed 1 Feb. 2017, the entire disclosures of which are incorporated herein in their entireties by this reference.

TECHNICAL FIELD

The present invention relates to an electromagnetic locking element for locking the joint of a joint orthosis or a joint prosthesis. Joint orthoses and joint prostheses generally feature a first and a second element that are connected to one another via a swivel joint such that they can be swivelled.

In particular, the present invention relates to a knee orthosis or a knee prosthesis. In this case, the first element can be arranged on the upper leg; the second element supports or replaces the lower leg.

BACKGROUND

Joint orthoses are used for patients who cannot control their knee joint or can no longer do so to a sufficient degree. Due to the fact that the swivel lock can be locked, such patients are still able to walk or stand. Specifically, the swivel joint can be locked in an extended position of the joint orthosis such that the orthosis ensures a secure standing position or a secure support when walking. Similarly, a joint prosthesis may replace a missing lower leg.

Such a joint orthosis is known, for instance, from the publication DE10311189 B4. Here, the locking occurs via a monostable solenoid with a pin, wherein said pin falls into the locked position due to gravity when no current is applied and can be moved out of the locked position by applying a voltage to a coil. This construction has the advantage that locking occurs automatically should the power supply fail. However, the construction has the disadvantage that it consumes more power due to the monostable construction. This considerably reduces the distance that can be covered by a patient with such a joint orthosis before the batteries in the orthosis much be recharged.

SUMMARY

The task of the present invention is thus to provide an improved electromagnetic locking element for a joint orthosis or joint prosthesis.

This task is achieved by way of an electromagnetic locking element according to the present disclosure. Additional configurations of the present invention are also disclosed herein.

The present invention comprises an electromagnetic locking element for stopping and/or separating general cargo carriers and/or general cargo that is/are transported on a continually operating general cargo conveyor system, comprising:

a bistable solenoid with at least one coil and at least one permanent magnet;
a pin, which can be retracted and extended with the aid of the solenoid,
one or several electrical energy stores, in particular capacitors,
a control system, which, with the aid of switches, discharges the energy store or energy stores via the at least one coil of the solenoid in such a way that the pin is extended.

The use of a bistable solenoid and the energy stores renders possible a very energy-efficient operation of the locking element.

In a possible embodiment of the present invention, the bistable solenoid features two stroke end positions. A first stroke end position preferably corresponds to the completely retracted position of the pin, and the second stroke end position corresponds to the completely extended position of the pin. In the completely extended position, the pin preferably locks the joint; in the completely retracted position preferably releases the joint.

A spring system is preferably provided, said system pre-loading one or several armatures of the bistable solenoid from the stroke end positions towards a central stroke position. The spring system increases the force of the solenoid and enables energy-efficient operation. The spring system may be installed in the solenoid or arranged externally to the solenoid as an additional component of the locking element.

Preferably, the amounts of potential energy stored in the locking element in the two stroke end positions, excluding the electrical energy and when no current is present, do not differ from one another by more than 50% of the greater value, preferably by no more than 25%. To calculate the potential energy, the electrical energy is discounted and the de-energized case observed. The potential energy thus initially results from the potential energy stored by the springs and permanent magnets. In the event that the pin is moved in the vertical direction, the potential energy of the pin due to gravity can also preferably be taken into account when calculating the potential energy stored in the locking element. Alternatively, the potential energy of the pin can however remain discounted.

A possible embodiment proposes that the bistable solenoid have an asymmetrical characteristic line. In particular, the force and/or acceleration of the solenoid during a movement out of the completely extended position of the pin may be greater than during a movement out of the completely retracted position.

A further embodiment proposes that the magnetic holding force of the solenoid is at its highest in the stroke end position in which the pin of the locking element is in its extended position.

This is preferably achieved by way of a geometric characteristic line modifier. Alternatively or additionally, the magnetic holding force in one of the stroke end positions may be between 20% and 80% of the magnetic holding force in the other stroke end position, preferably between 30% and 70%.

In a preferred embodiment, when no current is present, the locking element has a resting point at a position in which the pin is partially extended. Preferably, when at the resting point, the pin is extended sufficiently to lock the joint. This renders the structure considerably more secure.

The resting point may be achieved by way of an asymmetrical characteristic line.

The resting point is preferably offset in relation to the center of the stroke path, wherein the resting point is arranged specifically between the stroke end position, which corresponds to a completely extended position of the pin, and the center of the stroke path.

The distance between the resting point and the center of the stroke path is preferably greater than 5% of the stroke path, particularly preferably greater than 10%, especially preferably greater than 20%. Alternatively or additionally, the distance between the resting point and the stroke end position, which corresponds to completely extended position of the pin, is preferably greater than 2% of the stroke path, particularly preferably greater than 5%, especially preferably greater than 10%.

The resting point is preferably created by way of a resting point of the solenoid, in particular by way of a third stroke position of solenoid, said stroke position being stable when no current is present.

A possible embodiment proposes that the control system recognizes an interruption and/or switching off of the power supply of the locking element; in response to this, it extends the pin, wherein the failure of the supply voltage is preferably recognized by means of edge detection. The locking element can thus be controlled in exactly the same way as a locking element with a monostable solenoid.

Alternatively or additionally, the control system may be configured such that, in response to the switching on of the supply voltage, the electrical energy store or stores, preferably capacitors, is/are charged, and that said control system recognizes when a certain threshold voltage is reached in the electrical energy store; in response to this, said control system discharges the energy store or stores via the bistable solenoid in such a way that the pin is retracted.

In a possible embodiment, the bistable solenoid is controlled via a full bridge, in particular a MOSFET full bridge, wherein the full bridge preferably features two further switches, by way of which a first and a second energy store can be switched in parallel when in a first switch state, and discharged separately when in a second switch state.

In a possible embodiment, the control system has at least a first and a second electrical energy store, wherein the first energy store can be serially discharged via two coils of the solenoid, and wherein the second energy store can be discharged via only one of the two coils of the solenoid.

In a possible embodiment, the second energy store can be discharged via either of the two coils. In particular, the discharging may be conducted via the first or the second coil, depending on the direction of movement.

Alternatively or additionally, the second energy store may also be serially discharged via both coils of the solenoid. In particular, the discharging may be conducted via one of two coils or in series via the two coils, depending on the direction of movement.

Specifically, the electrical circuit can be configured in such a way that, in order to control a first direction of movement of the solenoid, in particular to extend the pin, both energy stores are serially discharged via the two coils of the solenoid, and to control a second direction of movement of the solenoid, in particular to retract the pin, the first energy store is serially discharged via both coils and the second energy store via only one of the two coils, especially via the first coil.

It is also beneficial if the discharging of the second energy store is conducted with a time delay in relation to the discharging of the first energy store, wherein the discharging of the second energy store preferably occurs prior to the start of the positioning cycle.

The solenoid preferably features two coils, which are switched in series and preferably have a center tap.

Furthermore, at least a first and a second energy store can be provided, wherein both energy stores are discharged via the serially switched coils along a first direction of movement, in particular in order to extend the pin, while in the opposite direction of movement, in particular to extend the pin, the first energy store is initially discharged via the serially switched coils, and the second energy store is discharged, with a time delay, via the center tap of both coils, wherein the discharging of the second energy store preferably occurs prior to the start of the positioning cycle.

In a possible embodiment, the control system features an instrument to measure the position of the locking element. In particular, the control system can take into account the positional information obtained by means of the position-measuring instrument when controlling the bistable solenoid. To this end, said control system preferably features a micro-controller, which is connected to the position-measuring instrument.

In a possible embodiment, the control system features an instrument for measuring the angular position of the joint, wherein the control system controls the locking element using the data obtained by the instrument for measuring the angular position. To this end, said control system preferably features a micro-controller, which is connected to the instrument for measuring the angular position. Preferably, the control system switches the supply voltage for the locking element on and off. This part of the control system may also be arranged in a higher-level control system of the joint orthosis or prosthesis, said higher-level control system controlling the control system of the locking element, in particular by switching the supply voltage on and off.

In a preferred embodiment, the energy stores of the control system are charged by way of a battery and/or a rechargeable battery. The battery and/or the rechargeable battery is/are preferably arranged on the joint orthosis or joint prosthesis and supplies/supply the supply voltage for the locking element.

Furthermore, the pin may comprise a damping mechanism and/or be connected to such a mechanism. The damping mechanism preferably brings the joint into the locked position, wherein the joint is damped during this process.

In a possible embodiment, the locking element comprises a spring system with a first spring, which, when in a first stroke end position, exerts a force on the armature or armatures towards the central stroke position, and a second spring, which, when in a second stroke end position, exerts a force on the armature or armatures towards the central stroke position, wherein the armature or armatures are held, permanently magnetized, against the spring force in both stroke end positions when no current is available. The spring system may be integrated into the solenoid or form a separate part of the locking element. The spring deflections of the first and second springs are preferably different in length and/or the first and second springs exert forces of different strength on the armature or armatures in the respective end position and/or have spring rates of different size.

As described above, the second stroke end position preferably corresponds to the completely extended position of the pin and the first stroke end position the completely retracted position.

The spring deflection of the first spring is preferably greater than the spring deflection of the second spring, and the second spring exerts a greater force on the armature or armatures when in the second stroke end position than the first spring exerts on the armature or armatures in the first stroke end position.

Alternatively or additionally, the spring deflection of the first spring may be greater than the spring deflection of the second spring, and the spring rate of the second spring in the second stroke end position greater than the spring rate of the first spring in the first stroke end position.

In a possible embodiment of the present invention, the spring deflection of the first spring is between 2-times and 100-times as large as the spring deflection of the second spring, preferably between 4-times and 20-times as large.

In another possible embodiment of the present invention, the force that the second spring exerts on the armature or armatures in the second stroke end position is between 1.5 times and 100-times as large as the force that the first spring exerts on the armature or armatures in the first stroke end position, preferably between 3-times and 15-times as large.

In another possible embodiment of the present invention, the spring rate of the second spring in the second stroke end position is between 2 times and 1000-times as large as the spring rate of the first spring in the first stroke end position, preferably between 10-times and 500-times as large, especially preferably between 20-times and 100-times as large.

In another possible embodiment, at least one of the springs and preferably the second spring does not generate a force between the armature and the stator across part of the stroke path and/or is not in contact with the armature and/or the stator across part of the stroke path. In this case, a restraint is preferably provided, which secures the spring in a predetermined position across this part of the stroke path, and preferably in a pre-loaded state.

A possible embodiment proposes that the magnetic holding force of the solenoid in one of the two stroke end positions is smaller than in the other stroke end position. In particular, the magnetic holding force of the solenoid in one of the two stroke end positions may be at least 20% smaller, preferably at least 30% smaller, than in the other stroke end position.

The magnetic holding force in the first stroke end position is preferably smaller than in the second stroke end position.

Alternatively or additionally, the magnetic holding force in one of the stroke end positions is at least 20% of the magnetic holding force in the other stroke end position, preferably at least 30%.

A possible embodiment proposes that the stator and the armature or armatures feature a geometric characteristic line modifier in one of the stroke end positions and preferably in the first stroke end position, in particular wherein said modifier is a working air gap, especially a conical working air gap, that does not run in a plane perpendicular to the axis of the solenoid.

The stator and the armature or armatures feature a weaker or no geometric characteristic line modifier in the other stroke end position and preferably in the second stroke end position.

A possible embodiment proposes that the difference between the value of the magnetic holding force and the value of the force applied by the respective spring in both stroke end positions differs by a maximum of 50% of the greater value.

In the following, a number of constructional characteristics of a solenoid are described as they can be applied in the locking element according to the invention. The characteristics may be realized on an individual basis or in combination with others.

A possible embodiment proposes that the at least one coil and the at least one permanent magnet are arranged on the stator.

A possible embodiment proposes that the stator forms a housing that encloses the armature or armatures, wherein one armature is preferably provided that is arranged on a guide rod inside the stator, wherein the guide rod is preferably moveably mounted on the stator. The guide rod is preferably connected to the pin and transmits the force of the solenoid to the pin.

A possible embodiment proposes that the spring system be arranged inside the stator, wherein the first spring is preferably arranged between the first front section and a first side of the armature, and the second spring is arranged between a second front section and a second side of the armature and/or wherein the first and the second spring are designed as spiral compression springs, which comprise the guide rods of the armature.

A possible embodiment proposes that the stator feature a magnetically soft casing, and a first and second magnetically soft front section, which form a housing in which the armature is arranged such that it can be displaced.

In a possible embodiment, at least a first working air gap may be provided between the armature and the first front section, and at least a second working gap between the armature and the second front section.

At least one permanent magnet and at least a first and a second coil are preferably arranged on the stator, wherein the armature forms a first port magnetic circuit with the casing and the first front section when in the first stroke end position, said pitch circle surrounding at least the first coil, while the working air gap or gaps with the second front section are opened to the maximum degree, and wherein the armature forms a second port magnetic circuit with the casing and the second front section when in the second stroke end position, said pitch circle surrounding at least the second coil, while the working air gap or gaps with the first front section are opened to the maximum degree.

A possible embodiment proposes that the at least one permanent magnet is arranged in the axial direction between the first and the second coil, each of which forms a part of the first and the second port magnetic circuit, wherein the permanent magnet is arranged in such a way that it overlaps with the armature in the axial direction in both the first and the second stroke end position and said magnet preferably surrounds the armature, wherein the permanent magnet preferably directly magnetically couples with the armature. However, other arrangements of the permanent magnet or permanent magnets are possible.

In contrast to this, a preferred embodiment proposes that at least a first and a second permanent magnet are provided, wherein the first and the second coil are arranged in the axial direction between the first and the second permanent magnet, wherein the first permanent magnet applies a magnetic voltage to the casing and the first front section and the second permanent magnet applies a magnetic voltage to the casing and the second front section. This allows for the structural length to be reduced in comparison to other structural designs.

A possible embodiment proposes that the first port magnetic circuit comprise the first permanent magnet and the second port magnetic circuit comprise the second permanent magnet.

A possible embodiment proposes that the armature magnetically short-circuits the casing and the first front section in the first stroke end position, and the armature magnetically short-circuits the casing and the second front section in the second stroke end position.

A possible embodiment proposes that the casing between the two coils feature a magnetic circuit section, which overlaps with the armature in the axial direction in both the first and the second stroke end position and which preferably surrounds said armature, wherein the magnetic circuit section preferably directly magnetically couples with the armature.

A possible embodiment proposes that the first and the second coil be at least partially arranged between the casing and the region of movement of the armature and/or in an inner groove and/or a recess of the casing.

Furthermore it proposes that preferably the first and/or second front section comprise a fixing region which extends in the radial direction beyond the first or second permanent magnet and is fixed to the casing. This renders assembly considerably easier. The fixing region is preferably saturated magnetically by way of the first or second permanent magnet.

In a possible embodiment, the fixing region is designed to be plate-shaped, in particular ring plate-shaped, and/or features recesses. In a possible embodiment, the fixing region comprises less material the further out it extends and in particular becomes thinner.

In a second independent aspect, the present invention includes a control system for the locking element as has been described above within the context of the locking element. In particular, the control system features switches, by way of which energy stores can be discharged via the at least one coil of the solenoid in such a way that the pin is extended. Here, the control system is preferably configured in the manner described above.

Specifically, in a possible embodiment, the control system has at least a first and a second electrical energy store, wherein the first energy store can be serially discharged via two coils of the solenoid, and wherein the second energy store can be discharged via only one of the two coils of the solenoid.

In a possible embodiment, the second energy store can be discharged via either of the two coils. In particular, the discharging may be conducted via the first or the second coil, depending on the direction of movement.

Alternatively or additionally, the second energy store may also be serially discharged via both coils of the solenoid. In particular, the discharging may be conducted via one of the two coils or in series via the two coils, depending on the direction of movement.

Specifically, the electrical circuit can be configured in such a way that, in order to control a first direction of movement of the solenoid, in particular to extend the pin, both energy stores are serially discharged via two coils of the solenoid, and to control a second direction of movement of the solenoid, in particular to retract the pin, the first energy store is serially discharged via both coils and the second energy store via only one of the two coils, especially via the first coil.

It is also beneficial if the discharging of the second energy store is conducted with a time delay in relation to the discharging of the first energy store, wherein the discharging of the second energy store preferably occurs prior to the start of the positioning cycle.

The present invention also comprises a joint orthosis or joint prosthesis with a first element and a second element, which are connected to one another via a swivel joint such that they can be swivelled, and with an electromagnetic locking element as described above for locking the swivel joint.

In particular, the locking element can used to lock the swivel joint in a first extended position of the joint orthosis or the joint prosthesis.

Here, the solenoid is preferably arranged on the first or second element, in particular in the region of the swivel joint.

Furthermore, the pin may interact with a locking element in order to lock the joint. The locking counterpart is preferably arranged on the other element, in particular in the region of the swivel joint.

In a possible embodiment, the joint orthosis or joint prosthesis features an instrument for measuring the angular position of the swivel joint, wherein the control system controls the locking element using the data obtained by the instrument for measuring the angular position. To this end, said control system preferably features a micro-controller, which is connected to the instrument for measuring the angular position. Preferably, the control system switches the supply voltage for the locking element on and off. The control system may represent a higher-level control system of the joint orthosis or prosthesis, said higher-level control system controlling the control system of the locking element, in particular by switching the supply voltage on and off.

In a preferred embodiment, the energy stores of the locking element are charged by way of a battery and/or a rechargeable battery. The battery and/or the rechargeable battery is/are preferably arranged on the joint orthosis or joint prosthesis, in particular on the same element as the locking element, and supplies the supply voltage for the locking element.

Specifically, the joint orthosis or joint prosthesis refers to a knee orthosis or knee prosthesis. In this case, the first element can be arranged on the upper leg; the second element supports or replaces the lower leg.

BRIEF DESCRIPTION OF THE DRAWINGS

The present invention will now be described in more detail with the aid of examples of embodiments and drawings.

They show.

DETAILED DESCRIPTION

Figure 1:
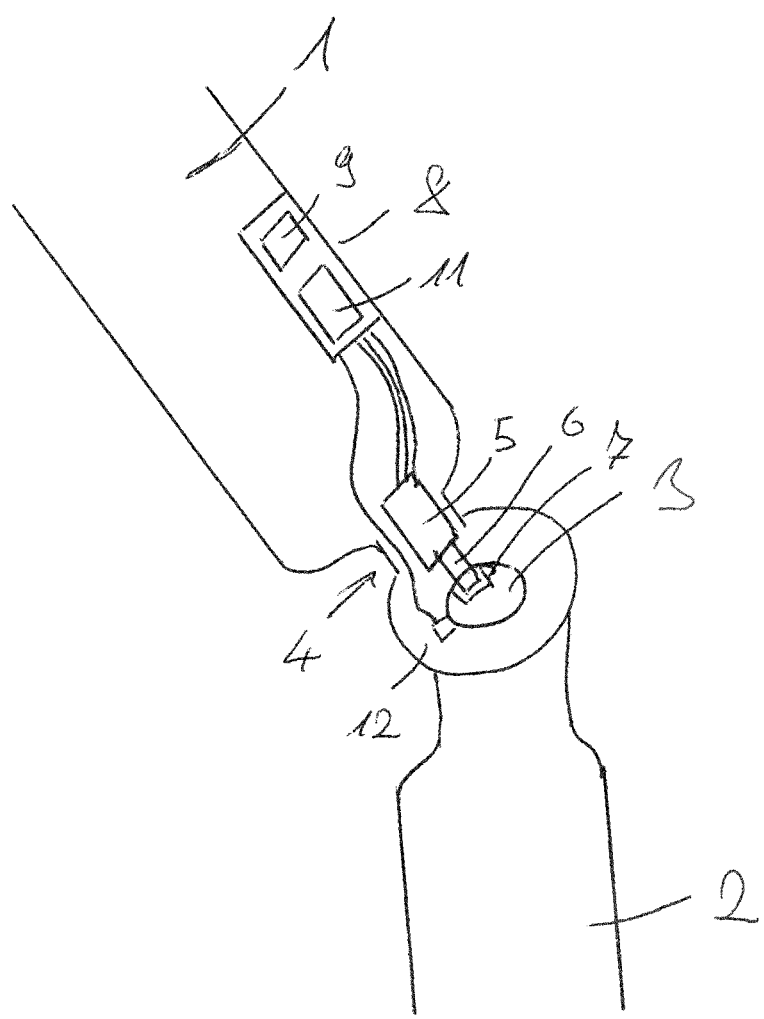
FIG. 1: an example of an embodiment of a joint orthosis or prosthesis according to the present invention.

FIG. 1 schematically depicts an example of an embodiment of a joint orthosis or prosthesis according to the invention. The joint orthosis or joint prosthesis features a first element 1 and a second element 2 that are connected to one another via a swivel joint 3 such that they can be swivelled. In particular, this refers to a knee orthosis or knee prosthesis. In this case, the first element 1 can be arranged on the upper leg; the second element 2 supports or replaces the lower leg.

The locking element 4 according to the invention is used to lock the swivel joint 3. To this end, it features a pin 6 that can be retracted and extended and that locks the swivel joint when in its extended position and releases the swivel joint when in its retracted position. To this end, a locking element 7 is provided which interacts with the pin 6 to lock the swivel joint. Within the meaning of the present invention, the retraction of the locking element does not require the pin to be retracted into a recess of a housing. Rather, a retraction has already occurred when the pin is moved from the extended position back into a position in which it releases the swivel joint.

Such joint orthoses are used for patients who cannot control their knee joint or can no longer do so to a sufficient degree. Due to the fact that the swivel lock can be locked, such patients are still able to walk or stand.

Specifically, the swivel joint can be locked in an extended position of the joint orthosis such that the orthosis ensures a secure standing position or a secure support when walking. Similarly, a joint prosthesis may replace a missing lower leg. To this end, the locking element and the locking counterpart are arranged in a corresponding position relative to one another on the first and the second element.

In a possible embodiment, several locking counterparts may be provided so the joint can be locked in different positions.

In the example of an embodiment, the locking element 4 is arranged on the first element 1; the locking counterpart is arranged on the second element 2.

The pin 6 is moveably arranged on the housing 5 of the electromagnetic locking element and according to the invention can be retracted and extended with the aid of a bistable solenoid. The housing is fixed to the first element. An axle 50 of the solenoid 10 is connected to the pin 6 in order to retract and extend said pin. Alternatively, the pin may be formed by an axle 50 of the solenoid.

Furthermore, a control system 8 is provided to control the solenoid 10. This features one or several electrical energy stores 9; in the example of an embodiment these are capacitors. Switches 11, semiconductor switches in the example of an embodiment, are also provided, which can discharge the energy store or energy stores 9 via a coil of the solenoid in such a way that the pin is extended.

The control system 8 preferably recognizes an interruption and/or switching off of the power supply of the locking element; in response to this, it extends the pin, wherein the failure of the power supply is preferably recognized by means of edge detection. Furthermore, the control system 8 may be configured such that, in response to the switching on of the power supply, the electrical energy store or stores is/are charged, and that the control system recognizes when a certain threshold voltage is reached in the electrical energy store; in response to this, said control system discharges the energy store or stores via the bistable solenoid in such a way that the pin is retracted.

In addition to the at least one coil, the solenoid comprises at least one permanent magnet and is configured to be bistable. Specifically, the solenoid is held, permanently magnetized, in both a first stroke end position, which corresponds to a completely retracted pin, and a second stroke end position, in which the pin is completely extended; this can only occur if the coils of the solenoid remain de-energized. The solenoid preferably features a spring system, which pre-loads the solenoid in the stroke end positions towards a central stroke position.

The joint orthosis or joint prosthesis also features a higher-level control system that controls the locking element, preferably by switching the supply voltage on and off. However, a direct control of the switches of the control system of the locking element is also conceivable. The supply voltage for charging the energy stores, in particular the capacitors, is preferably provided by way of batteries and/or rechargeable batteries. Said batteries and the control system of the joint orthosis or joint prosthesis are preferably arranged on the first element.

In the example of an embodiment, a sensor 12 is also provided which measures the angular position of the swivel joint. The data from the sensor 12 can be evaluated via the control system of the joint orthosis or joint prosthesis and used to control the locking element.

In the example of an embodiment, when no current is present, the locking element has a resting point at a position in which the pin is partially extended. Specifically, this is achieved via another stable stroke position of the solenoid, which lies between the first and second stroke end position. Preferably, when at the resting point, the pin is extended sufficiently to lock the swivel joint. In particular, the pin can be extended beyond its central position and preferably extended to at least 70% of its stroke path.

An example of an embodiment of a bistable solenoid, as it may be used within the scope of the present invention, as well as two examples of an embodiment of control systems for controlling a solenoid according to the invention are explained in the following in more detail with the aid of FIGS. 2 to 4.

Figure 2:
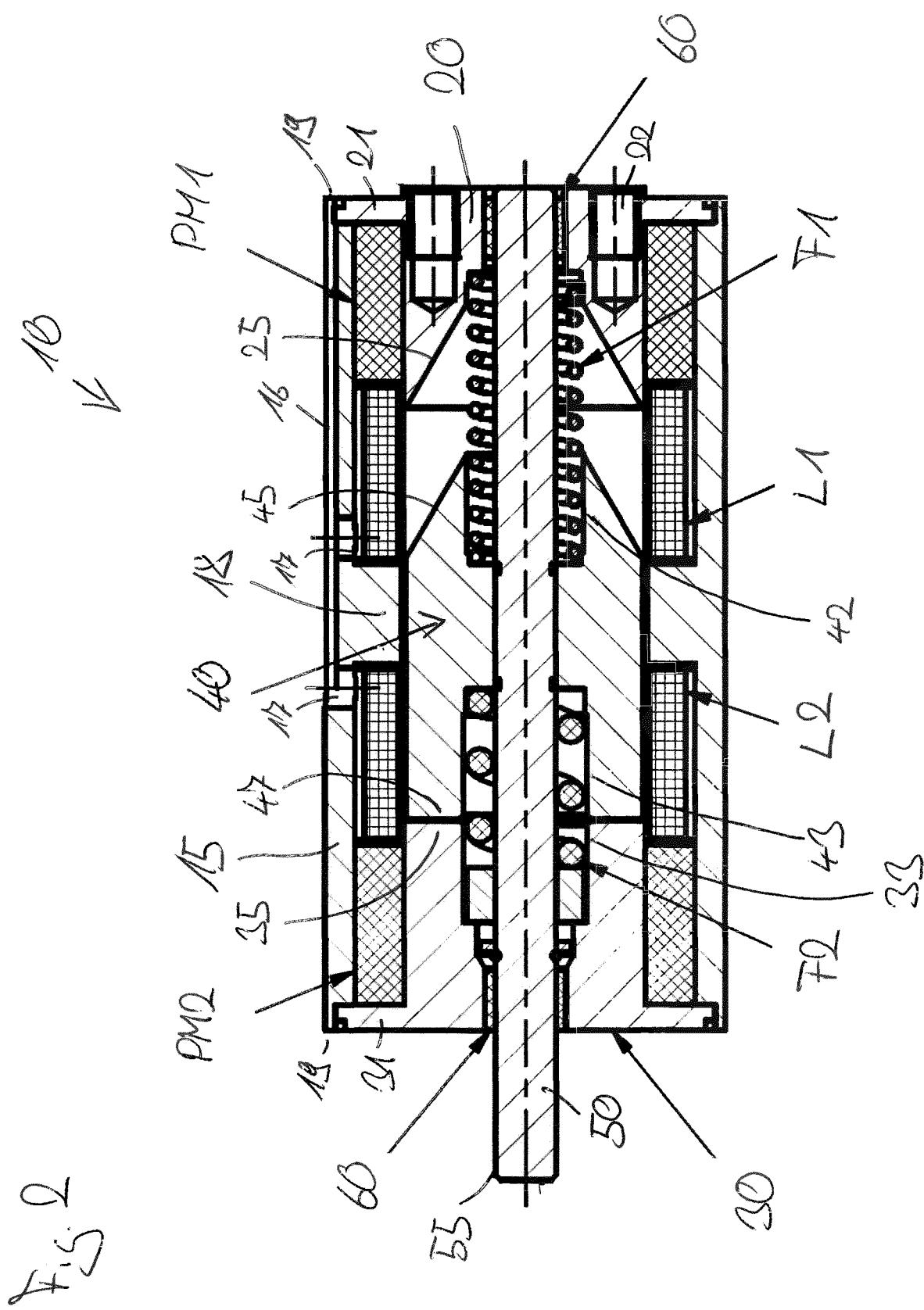
FIG. 2: a example of an embodiment of a solenoid according to the invention in a sectional view.

FIG. 2 shows an example of an embodiment of a bistable solenoid which features a combination of a plurality of aspects of the present invention. However, in accordance with the individual aspects, the combination of characteristics described with the aid of the example of an embodiment may also be used in their own right according to the invention.

The bistable solenoid according to the present invention has a stator and an armature 40 that can be axially displaced in relation to the stator. The stator and armature are made of a magnetically soft material.

In the example of an embodiment, the stator comprises a magnetically soft casing 15 and two magnetically soft front sections 20 and 30, which form a housing in which the armature 40 is arranged such that it can be displaced. In the example of an embodiment, the front sections each feature an area that is arranged in the casing 15, in particular a fundamentally cylindrical area.

In the example of an embodiment, the armature 40 is borne by an axle 50, which is mounted by way of bearings 60 on the front sections 20 and 30 of the stator such that it can be axially displaced. A movement of the armature 40 also moves the axle 50. In the example of an embodiment, the axle 50 features a second side with a connection area 55, which can be connected to the pin. Alternatively, the axle 50 may directly serve as the pin, wherein the area 55 preferably interacts with a locking counterpart. The working air gaps of the solenoid are preferably located between the armature 40 and the front sections 20 and 30.

In the second stroke end position, the second side of the axle 50 with the connection area 55 is fully extended so that the pin is also fully extended. In the first stroke end position, the second side of the axle 50 with the connection area 55 to the pin is completely retracted and the axle on the opposite first side completely extended. In the first stroke end position the pin is completely retracted.

In the example of an embodiment, the solenoid features bores 22, especially threaded bores, by way of which it is mounted on the joint orthosis or prosthesis.

Alternative structural designs of the stator, the armature and the axle are also conceivable within the scope of the present invention.

The interior structure of the solenoid is shown in the sectional view in FIG. 2. The bistable solenoid has a spring system with a first spring F1, which exerts a force on the armature 40 towards the central stroke position when in a first stroke end position, and a second spring F2, which exerts a force on the armature 40 towards the central stroke position when in the second stroke end position shown in FIG. 2.

In the example of an embodiment, both springs are arranged inside the housing formed by the stator between one of the front sections 20 or 30 and the armature 40. In the example of an embodiment, such springs are spiral springs which surround the axle 50. Ring grooves 42 and 43 are provided in the armature 40, wherein said ring grooves accommodate at least one part of the respective spring when in the respective stroke end position. Corresponding ring grooves may also be provided in the front sections 20 and 30.

Furthermore, at least one permanent magnet PM1 and PM2 is provided, which holds the armature 40 in the respective stroke end position against the force of the respective spring when no current is present. In the example of an embodiment, two permanent magnets PM1 and PM2 are provided, which are allocated to the respective stroke end positions. A single permanent magnet may also be used instead of two permanent magnets.

Coils L1 and L2 are also provided; by supplying said coils with power, the armature can be driven from one stroke end position into the other stroke end position. In the example of an embodiment, two coils L1 and L2 are provided, the coils of which are guided separately out of the housing in area 17. Alternatively, the coils may also be switched in order inside the housing and preferably comprise a center tap.

According to the first aspect of the present invention, different springs F1 and F2 are used. In the example of an embodiment, the first and the second spring feature spring deflections that are different in length. In particular, the spring deflection of the first spring F1 is greater than the spring deflection of the second spring F2. Furthermore, both springs exert forces of different strength on the armature in the respective stroke end positions. Specifically, when in the first stroke end position, in which the armature 40 reaches the first front section 20, the first spring F1 exerts a smaller force on the armature 40 than the second spring 40 when in the second stroke end position depicted in FIG. 2, in which the armature 40 reaches the second front section 30. In the example of an embodiment, the first spring F1 also has a smaller spring rate than the second spring F2.

Furthermore, due to the smaller spring deflection, the second spring only exerts a force on the armature 40 across one part of the stroke path. A restraint—not depicted in FIG. 2—is preferably provided which secures the second spring F2 in a predetermined position and in a pre-loaded state across the part of the stroke path in which said spring does not generate any force between the armature and the stator. This increases the operating life of the solenoid.

In the concrete example of an embodiment, the solenoid has a stroke path of 15 mm. The first spring has a spring deflection that is equivalent to the stroke path. In contrast to this, the second spring F2 has a spring deflection of only 2 mm. In the first stroke end position, the first spring exerts a force of approximately 5 N on the armature and has a spring rate of approximately 0.35 N/mm. In the second stroke end position, the second spring exerts a force of approximately 35 N on the armature and has a spring rate of approximately 17 N/mm. Both springs are pre-loaded upon reaching their maximum spring deflection.

In the example of an embodiment, the different springs F1 and Fr can be used to achieve a number of advantages. The strong spring F2 ensures a high acceleration of the armature during a movement from the second stroke end position towards to the central stroke position. In contrast to this, first spring F1 with the long spring deflection enables a correspondingly long configuration of the stroke path.

According to another aspect of the present invention, the solenoid has an asymmetrically arranged resting point when no current is present. This resting point represents a third stable stroke position of the bistable solenoid when no current is present, said position being arranged between the first and the second stroke end position. This resting point, in which the opposing forces exerted by the springs and permanent magnets on the armature 40 offset one another, is asymmetrical, i.e. arranged at an offset in relation to the center of the stroke path.

This has the advantage that only a small amount of energy is needed to bring the solenoid into a largely extended or retracted position; this is achieved by driving said solenoid from the stroke end position that is further away from the resting point into the resting point. Such an asymmetrical resting point, which can be achieved by supplying only a small amount of energy, represents an important safety function in many applications.

In the example of an embodiment, the asymmetrical resting point is primarily achieved by way of the different springs in accordance with the first aspect of the present invention, in particular by way of the spring deflections of different length and/or the forces of different strength and/or the spring rates of different size of the first and the second spring. In particular, the resting point is arranged closer to the second stroke end position than the first stroke end position, as the second spring has a smaller spring deflection than the first spring. Given that the second spring has a considerably larger spring rate than the first spring, the resting point is predominantly determined by the length of the spring deflection of the second spring and therefore lies at a distance of approximately 2 mm from the second stroke end position in the example of an embodiment. In the example of an embodiment, the magnetic forces acting on the armature only play a subordinate role with regards to the exact position of the resting point.

Only a small amount of energy is required to reach the resting point from the first stroke end position, as the (considerable) resetting force of the second spring F2 need not be overcome to do so. Nevertheless, the drive has already been largely extended upon reaching the resting point.

According to another aspect of the present invention, the solenoid is designed such that the permanent magnetic holding force, often described as the "adhesive force", is different in the first and second stroke end position. In particular, the solenoid is configured in such a way that the permanent magnetic holding force in the first stroke end position is smaller than in the second stroke end position. To this end, in the example of an embodiment a geometric characteristic line modifier is provided between the first front section 45 of the armature, which faces the first front section 20, and the inner side 25 of the first front section 20. The first working air gap is situated between these two surfaces 25 and 45, said working air gap being closed in the first end position. The geometric characteristic line modifier means that the surfaces 25 and 45 do not run in a plane perpendicular to the axial direction of movement of the solenoid, but rather feature a profile in relation to such a plane. In the example of an embodiment, the surfaces have a conical profile, which, in the example of an embodiment, has an angle that reduces the permanent magnetic holding force by approximately 50%.

On the opposite side however, on which the second front section 47 of the armature 40 and the inner side 35 of the second front section 30 lie opposite one another across a second working air gap, no geometric characteristic line modifier is provided. Here, the two surfaces, between which the working air gap is situated, run in a plane perpendicular to the axial direction of movement of the solenoid.

The permanent magnetic holding forces of different strength in the first and the second stroke end position are preferably selected in such a way that the respective difference between the permanent magnetic holding force and the respective opposing spring force is generally of equal size in both stroke end positions and/or preferably lies in at least the same scale when taking into account external forces acting on the solenoid. This difference safeguards the solenoid in both stroke end positions against inadvertent release, for example caused by vibrations. In the example of an embodiment, the magnetic holding force in the first stroke end position is approximately 25 N; in the second stroke end position, it is approximately 50 N.

According to another aspect of the present invention, the bistable solenoid is designed in such a way that the values of the potential energy stored in the solenoid in the two stroke end positions do not differ from one another by more than 50% of the greater value, i.e. the smaller of the two values is at least 50% of the greater value. Here, the potential energy of the two stroke end positions is generally the same. To calculate the potential energy, the electrical energy is discounted and the de-energized case observed. In the most simple case, the potential energy results from the potential energy stored by the springs and permanent magnets.

It is especially preferable if, within the scope of determining the potential energy, external forces are taken into account, which act on the bistable solenoid within the scope of its specific use. For instance, this may be the force of gravity when the solenoid raises an element against the force of gravity. Alternatively or additionally, this may also refer to external spring forces, for example if the solenoid is used to move a spring-loaded element.

Given that the amount of potential energy in both stroke end positions is similar, operation of the solenoid is especially energy-efficient. In the example of an embodiment, the similar amounts of potential energy are achieved in particular thanks to the fact that the spring has the same spring deflection with the greater force and/or spring rate.

In the example of an embodiment of the bistable solenoid shown in FIG. 2, a second aspect of the invention is realized, said aspect being independent of the above aspects and especially of the different configuration of the springs; said aspect differs in the structural design of the stator, the armature and the arrangement of the permanent magnets and coils.

In the example of an embodiment, the stator is formed by a magnetically soft casing 15 and the two front sections 20 and 30, which together form a housing, inside of which the magnetically soft armature 40 is arranged such that it can be displaced. The casing 15 extends between the first front section 20 and the second front section 30 across the entire length of the solenoid. A first working air gap is formed between the first side of the armature 40 and the first front section 20; a second working air gap is formed between the second side of the armature 40 and the second front section 30.

According to the second aspect, two permanent magnets PM1 and PM2 are provided, which hold the armature 40 in the respective stroke end position against the force of the spring system. Both permanent magnets PM1 and PM2 are arranged between the magnetic casing 15 and the respective front section 20 or 30 such that they are subjected to a magnetic voltage. To this end, PM1 and PM2 may be formed, for instance, of one or several radially polarized, magnetically hard rings, preferably NdFeB. Alternatively, PM1 and PM2 are formed of radially or diametrically polarized, magnetically hard ring segments. In the respective end position, the armature 40 short-circuits the casing 15 with the respective front section 20 or 30 across the magnetic circuit section 18, which acts as a return path, such that the respective permanent magnet exerts a holding force on the armature 40 in the respective end position. A coil L1 or L2 is allocated to each of the two end positions; by supplying said coils with power, the armature can be released from the respective end position or, in the reverse current direction, pulled into its end position against the force of the respective spring.

The port magnetic circuit, formed in the first or second end position by the casing, the armature, the respective front section and respective permanent magnet, surrounds the respective coil L1 or L2 in such a way that, when the coil is supplied with power in a current direction, this power acts against the magnetic holding force of the respective permanent magnet and thus ensures a displacement of the armature out of the respective end position. If the holding force of the permanent magnet is overcome, the respective spring makes a considerable contribution to the movement of the armature.

The coils L1 and L2 are arranged in the axial direction of the solenoid between the two permanent magnets PM1 and PM2. The casing 15 features a central magnetic circuit section 18, which is arranged between the two coils L1 and L2 such that it magnetically couples with the armature 40 in both the first end position and the second end position. The coils L1 or L2 connect to both sides of this magnetic circuit section 18 of the casing 15 in the axial direction; the respective permanent magnets PM1 and PM2 are then arranged alongside said coils further out in the axial direction. In the example of the embodiment, the magnetic circuit section 18 is formed by an elevation of the inner wall of the casing 15, said elevation protruding inwards, while the coils L1 and L2 or the permanent magnets F1 and F2 are arranged in grooves or recesses on the inner circumference of the casing 15.

In the example of an embodiment, the permanent magnet PM1 and PM2 are each arranged between the casing 15 and a part of the respective front section 20 or 30 that protrudes into the casing. In contrast to this, the coils L1 and L2 are at least partially arranged alongside the region of movement of the armature 40.

The use of the permanent magnets PM1 and PM2, which are arranged axially outwards, enables the structural length of the solenoid to be reduced, which is not the case with other structural models.

In the example of an embodiment, the solenoid is configured about the axle 50; this is conducted in a rotationally symmetrical manner.

According to a further aspect of the present invention, the magnetically soft front sections 20 and 30 of the stator each feature a fixing area 21 or 31, by way of which they are connected to the casing 15. In structural terms, this has considerable advantages as it enables a simple and stable connection between the front sections and the casing in the connection area 19.

However, given that the fixing area 21 or 31 extends in the radial direction across the first or second permanent magnet PM1 or PM2, it actually creates an inadvertent magnetic short-circuit between the casing and the respective front section. The fixing area is thus preferably configured such that it is completely magnetically saturated by the respective permanent magnet. The magnetic flow that flows from the casing across the fixing section is preferably a maximum of 50% of the magnetic flow that flows from the casing via the armature to the respective front section, preferably a maximum of 20%, when in the respective end position.

The fixing area 21 or 31 is designed to be panel-shaped, in particular ring plate-shaped. The fixing area may also comprise recesses in order to reduce the magnetically soft material in the region of the fixing area. In a possible configuration, the fixing area 31 may feature less material further outwards, for instance by being designed to be thinner further outwards, in order to effect as even a saturation as possible in this area.

In the example of the embodiment, the first and second aspect are realized in combination with one another, i.e. the solenoid has a structural design according to the second aspect as well as different springs according to the first aspect. The remaining aspects described above are also realized in combination with one another.

However, each one of the aspects of a solenoid described above according to the present invention can also be realized independently of the other aspects. The characteristics described for each individual aspect therefore also embody the present invention independently of the other characteristics described for the other aspects. Furthermore, only some of the aspects can be combined with one another, wherein the present invention includes all combinations of the aspects describe above.

In particular, the structural design according to the second aspect can also be used with identical springs and/or identical magnetic holding forces.

Furthermore, the configuration with different springs and/or different magnetic holding forces and/or an asymmetrical resting point can also be used with a different structural design of the holding magnet.

For example, instead of the two outwardly lying permanent magnets PM1 and PM2, a single permanent magnet arranged in the region of the magnetic circuit section 18 can be used, said single permanent magnet applying a magnetic voltage to the casing 15 and the armature 40 in both end positions.

Other structural designs of the stator are also conceivable, for example with two separate magnetically soft sections, between which at least parts of the armature are arranged, for instance in the form of an armature plate. Alternatively or additionally, configurations with outwardly lying armature plates and/or permanent magnets that are also arranged on the armature are also conceivable.

Figure 3:
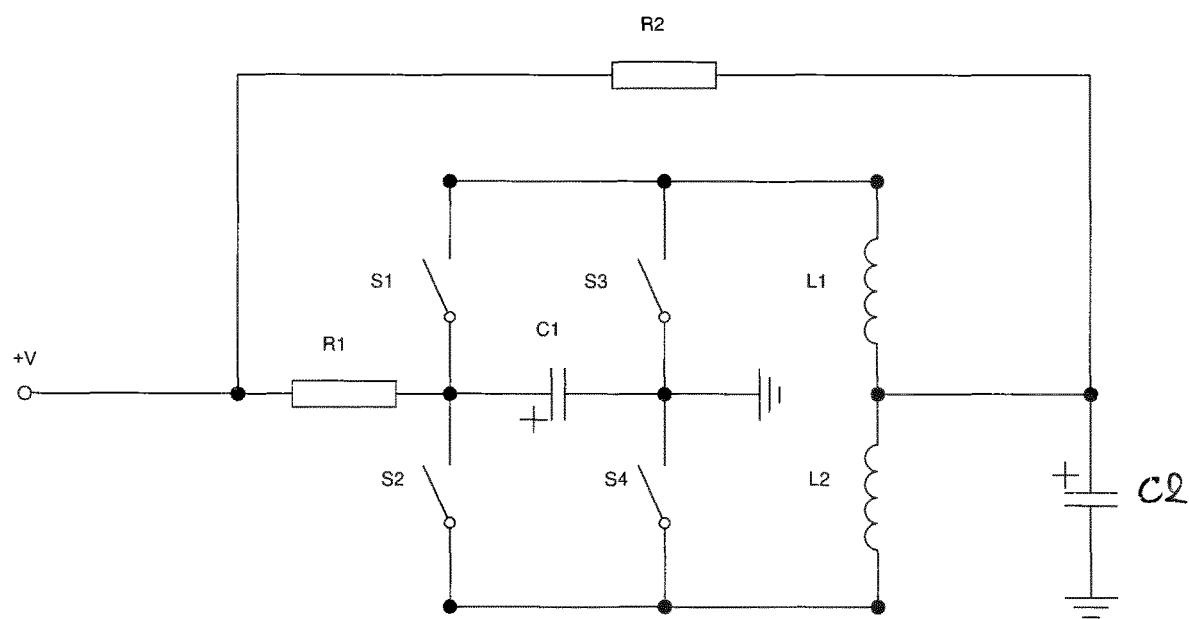
FIG. 3: a first example of an embodiment of a control system for controlling the bistable solenoid according to the invention.
Figure 4:
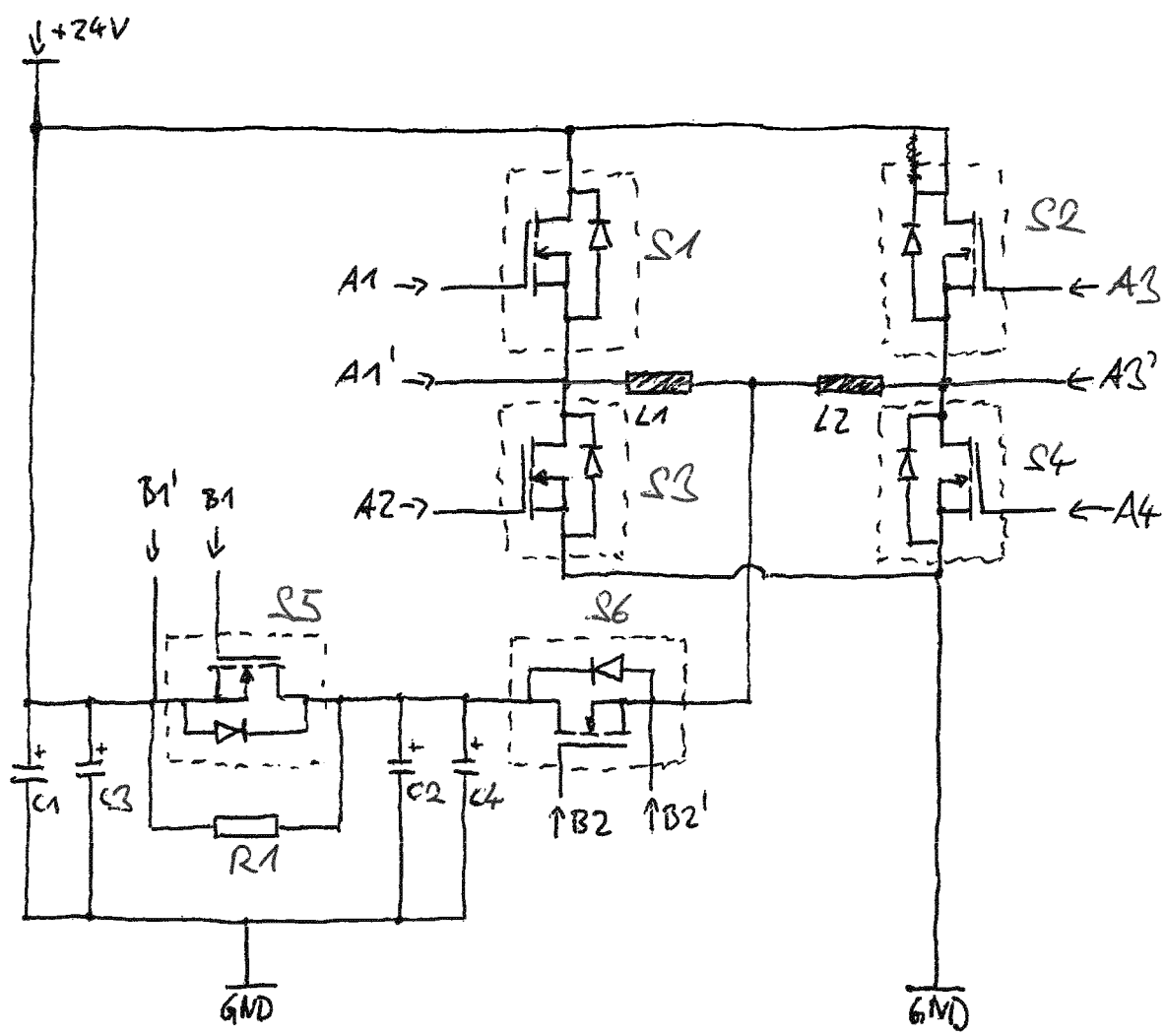
FIG. 4: a second example of an embodiment of a control system for controlling the bistable solenoid according to the invention.

Possible configurations of a control system for controlling a bistable solenoid within the scope of the present invention are depicted in FIGS. 3 and 4. They can be used to control any desired bistable solenoids, which feature at least two coils L1 and L2. It is especially preferable if the control system is used for bistable solenoids whose armature is held, permanently magnetized, in the first and second stroke position when no current is present, wherein, by supplying the first coil L1 and/or the second coil L2 with power in a first current direction, the solenoid is released from the first end position and, by supplying the second coil L2 and/or the first coil L1 with power in a second current direction, the solenoid is released from the second end position.

It is especially preferable if the solenoid has a spring system with a first and a second spring, wherein the first spring exerts a force on the armature towards to central position when in the first end position, and the second spring exerts a force on the armature towards to central position when in the second end position. By supplying at least the first coil L1 with power in a second current direction, the solenoid can be pulled into the first end position against the spring force of the first spring; by supplying at least the second coil L2 with power in a second current direction, the armature can be pulled into the second end position.

In the respective end position, the stator and the armature form a port magnetic circuit that surrounds the respective coil L1 or L2, such that the permanent magnetic holding force is weakened when the respective coil is supplied with power in the first current direction.

It is especially preferable if the control systems can be used to control a solenoid according to the invention, as described above; in particular, it is preferable if said control systems can be used to control a solenoid in which one or several of the aspects described above are realized. Furthermore, the solenoids according to the invention described above preferably function in the way described away.

Common to both examples of an embodiment of the control system is the fact that the coils L1 and L2 are supplied with power via one or several energy stores C1, C2, which are discharged by way of the switches S1 to S4 via the coils L1 and L2. In the example of an embodiment, the energy stores refer to capacitors, in particular electrolyte capacitors. To this end, a full bridge formed by the switches S1 and S4 is used in the example of an embodiment in order to be able to freely select in which switch discharging occurs via the coils.

Common to both examples of an embodiment is the fact that at least a first energy store C1 can be discharged via the consecutively switched coils L1 and L2. In contrast to this, at least a second energy store C2 can be discharged via only one of the two coils L1 or L2. To this end, the second energy store C2 can be connected to the center tap between the two coils L1 and L2. The full bridge determines which of the two coils L1 or L2 is used for the respective discharging, wherein said full bridge is used to control the discharge direction of the first energy store C1 and to control the discharging of the second energy store C2 via the first coil L1 or the second L2.

In the example of an embodiment shown in FIG. 3, the energy store C2 is constantly connected with the center tap between the two coils. If the discharging is enabled by the full bridge, the first energy store serially discharges via the two coils L1 and L2 and the second energy store C2 via one of the two coils L1 and L2; this occurs simultaneously.

In contrast to this, in the example of an embodiment shown in FIG. 4, the energy store C2 is connected with the center tap between the two coils L1 and L2 such that it can be switched, which is achieved via the switches S6. In contrast to this, a further switch S5 can be used to switch the second energy store C2 in parallel to the first energy store C1.

In a first operating mode, the circuit in FIG. 4 can serially discharge both energy stores C1 and C2 via the two coils L1 and L2. In contrast to this, in a second operating mode, only the first energy store C1 is serially discharged via the coils L1 and L2; the second energy store C2 is discharged via one of the two coils L1 or L2. Preferably, in the second operating mode the second energy store C2 is switched at a time offset in relation to the full bridge, i.e. the second energy store C2 is first connected with the center tap between the two coils after the full bridge has already created a connection between the first energy store and the two coils, and the electrical circuit has been closed to discharge C1. However, the second energy store C2 is preferably switched at an early enough point that the positioning movement has not yet commenced.

The discharging of the second energy store C2 via the center tap results in said energy store only being discharged via one of the two coils L1 or L2. This means that more energy is available for this coil. A further advantage is that the energy is restricted by the other coil, meaning that an overcompensation is prevented.

The circuit is preferably configured such that the first operating mode is used to move the solenoid in a first direction and the second operating mode is used to move the solenoid in a second direction. In particular, the first operating mode, in which both energy stores C1 and C2 are switched in parallel and both are discharged via the serially switched coils L1 and L2, can be used for a movement from the first stroke end position into the second stroke end position, i.e. to extend the pin. Conversely, for a movement from the second stroke end position into the first stroke end position, i.e. to retract the pin, the second operating mode is preferably used, in which the second energy store C2 is discharged parallel to the energy store C1 via one of the two coils L1 and L2, preferably with a time offset in relation to the discharging of the first energy store C1. Such a different control of the two directions of movement is especially advantageous if the solenoid features an asymmetrical characteristic line and/or different springs.

The switches of the full bridge and the switches for switching between the first and second operating modes are preferably designed as semiconductor switches, particularly in the form of a MOSFET.

This is depicted in FIG. 4. Control inputs A1 to A4 and B1 and B2 are provided for control purposes, wherein a voltage difference in relation to the reference ports A1', A3', B1 and B2' is set via said inputs for the control of the respective switch.

In the example of an embodiment in FIG. 4, two first energy stores C1 and C3 and two second energy stores C2 and C4 are also switched in parallel to one another.

In the example of an embodiment shown in FIG. 3, the charging of the energy stores C1 and C2 is achieved via resistors R1 and R2, by way of which said energy stores are connected to a power supply +V. If a power supply is switched on, the energy stores are charged via the respective resistors.

However, in both the first and second example of an embodiment, an electronically controlled charging of the energy stores preferably occurs, in particular using a constant loading current.

Alternatively or additionally, the loading current, by way of which the energy stores are charged, is adjustable. For example, the control system may have several operating modes, which differ in the size of their loading current, wherein the control system can preferably be switched between the operating modes. The required dead time between two positioning cycles is largely determined by the loading current. In the event of a high loading current, the time required between two positioning cycles is reduced. Conversely, a lower loading current increases the time. As a result of the different operating modes, the solenoid may be operated using an energy supply with a lower output without overburdening said energy supply if, for example, longer periods between two positioning cycles are permitted.

Different loading currents can be realized, for example, by way of different resistors or a corresponding electronic control system, preferably by way of switching regulators, such as a step-up or step-down converter.

Independently of the specific configuration of the control system as described above, the solenoid according to another aspect of the present invention is controlled in such a way that, upon switching off the power supply, the solenoid is moved from the first into the second stroke end position. Conversely, upon switching on the power supply, the solenoid is moved back from the second stroke end position into the first stroke end position.

The supply voltage is preferably monitored. For example, a failure of the supply voltage can be recognized by means of edge detection. If the supply voltage fails, the energy stores are discharged via the coil or coils of the solenoid in order to move the solenoid from the first into the second stroke end position.

Preferably, after switching on the supply voltage, the electrical energy store is initially charged, wherein the control system recognizes when a certain threshold voltage is reached in the energy store; in response to this, said control system discharges the energy store via the coil or coils of the solenoid in such a way that said solenoid moves from the second into the first stroke end position.

Such a configuration has the advantage that the solenoid according to the invention can be easily used as a replacement for monostable solenoids.

If the solenoid features a resting point that is offset in relation to the central position as described above, such an operation is particularly secure. As a result, even if the supply voltage inadvertently fails very shortly after a switching cycle, during which the solenoid was driven into the first stroke end position, or other such problems occur in the energy stores, it is still possible to drive it into the resting point, as this requires very little energy. However, when at this resting point, the solenoid has already been largely extended towards to second stroke end position.

This considerably increases the degree of safety when a bistable solenoid is used to retract and extend the pin.

We claim:

1. An electromagnetic locking element for locking a joint orthosis or joint prosthesis, comprising:
    a bistable solenoid with at least one coil and at least one permanent magnet;
    a pin, which can be retracted and extended with the aid of the solenoid for locking the joint;
    at least one electrical energy store;
    an electrical control system, which, with the aid of semiconductor switches, discharges the at least one energy store via the at least one coil of the solenoid in such a way that the pin is extended; and
    a spring system with a first spring, which exerts a force on an armature towards a central stroke position when in a first stroke end position, and a second spring, which exerts a force on the armature towards the central stroke position when in a second stroke end position, wherein the armature is held, permanently magnetized, against the spring force in both stroke end positions when no current is present, wherein at least one of spring deflections of the first and second springs are different in length, and wherein the first and second springs exert forces of different strength on the armature or have spring rates of different size, wherein the spring deflection of the first spring is greater than the spring deflection of the second spring.

2. The locking element according to claim 1, wherein the bistable solenoid has two end positions.

3. The locking element according to claim 2, wherein amounts of potential energy stored in the locking element in the two end positions, excluding the electrical energy and when no current is present, do not differ from one another by more than 50% of a greater of the stored potential energies.

4. The locking element according to claim 1, wherein at least one of the bistable solenoid has an asymmetrical characteristic line and the magnetic holding force of the solenoid is highest in the end position in which the pin of the locking element is extended, which is reached by way of at least one of a geometric characteristic line modifier and the magnetic holding force in one of the end positions is between 20% and 80% of the magnetic holding force in the other end position.

5. The locking element according to claim 1, wherein the locking element has a resting point at a position in which, when no current is present, the pin is partially extended, wherein at least one of the pin, at the resting point, is extended sufficiently to lock the joint, wherein the bistable solenoid has an asymmetrical characteristic line and the resting point is at least partially formed by the asymmetrical characteristic line, and the resting point is offset relative to the center of a stroke path, wherein at least one of the resting point is arranged between a stroke end position that corresponds to a completely extended position of the pin and a center of a stroke path, a distance between the resting point and the center of the stroke path is greater than 5% of the stroke path, and the distance between the resting point and the stroke end position that corresponds to a completely extended position of the pin is greater than 2% of the stroke path.

6. The locking element according to claim 1, wherein the control system at least one of recognizes an interruption and extends the pin in response to switching off of a power supply of the locking element, wherein a failure of the supply voltage is recognized by edge detection.

7. The locking element according to claim 1, wherein the control system is configured such that, in response to a switching on of a supply voltage, the at least one electrical energy store is charged, and that the control system recognizes when a certain threshold voltage is reached in the at least one electrical energy store, and in response the control system discharges the at least one electrical energy store via the bistable solenoid in such a way that the pin is retracted.

8. The locking element according to claim 1, wherein the bistable solenoid is controlled via a full bridge, wherein the full bridge includes two further switches, by way of which a first and a second electrical energy store of the at least one electrical energy store can be switched in parallel when in a first switch state, and discharged separately when in a second switch state.

9. The locking element according to claim 1, wherein the at least one electrical energy store includes a first and a second electrical energy store, wherein the first energy store can be serially discharged via two coils of the solenoid, and wherein the second energy store can be discharged via one of the two coils of the solenoid, wherein the second energy store can be discharged via at least one of one of the two coils and serially via two coils of the solenoid, wherein the electrical circuit is configured such that, in order to control a first direction of movement of the solenoid, both energy stores are serially discharged via two coils of the solenoid, and in order to control a second direction of movement of the solenoid, the first energy store is serially discharged via the coils and the second energy store via only one of the two coils, wherein the discharging of the second energy store occurs with a time delay in relation to the discharging of the first energy store, wherein the discharging of the second energy store occurs before a positioning cycle begins, or the two coils, which are switched in series and have a center tap, wherein both energy stores are discharged via consecutively switching the two coils along a first direction of movement, while in an opposite direction of movement, the first energy store is initially discharged via the consecutively switched coils, and the second energy store is discharged, with a time delay, via the center tap of both coils, wherein the discharging of the second energy store occurs before the positioning cycle begins.

10. The locking element according to claim 1, further comprising at least one of an instrument for measuring the position of the locking element and an instrument for measuring the angular position of the joint, wherein the control system takes into account positional information obtained by the position-measuring instrument for at least one of the control of the bistable solenoid and controls the locking element with the aid of data obtained using the instrument for measuring the angular position, wherein the control system comprises a micro-controller, which is connected to at least one of the position-measuring instrument and the instrument for measuring the angular position, or wherein the energy store is at least one of charged via a battery and a rechargeable battery.

11. The locking element according to claim 1, wherein the second stroke end position represents a completely extended position of the pin and the first end position is a completely retracted position, and the second spring exerts a greater force on the armature when in the second stroke end position than the first spring exerts on the armature in the first stroke end position, or wherein the spring deflection of the first spring is greater than the spring deflection of the second spring, and the spring rate of the second spring in the second stroke end position is greater than the spring rate of the first spring in the first stroke end position.

12. The locking element according to claim 1, further comprising a stator, wherein the stator and the armature each have a geometric characteristic line modifier in one of the first and second stroke end positions, wherein a modifier is a working air gap that does not run in a plane perpendicular to an axle of the solenoid, wherein the stator and the armature have a weaker or no geometric characteristic line modifier in the other first and second stroke end position, wherein a difference between a value of the magnetic holding force and a value of the force applied by the respective first and second spring in both first and second stroke end positions differs by a maximum of 50% of a greater of the force applied.

13. The locking element according to claim 1, further comprising a stator and at least one permanent magnet, wherein the stator includes a magnetically soft casing, and a first and second magnetically soft front section, which form a housing in which the at least one armature is arranged such that it can be displaced, wherein at least a first working air gap is provided between the at least one armature and the first front section, and at least a second working air gap between the at least one armature and the second front section;

wherein at least one permanent magnet and at least a first and a second coil are arranged on the stator, wherein, when in the first stroke end position, the at least one armature forms a first port-magnetic-circuit with the casing and the first front section, a first port-magnetic-circuit surrounding at least the first coil, while the working air gap with the second front section are opened to a maximum degree; and wherein, when in the second stroke end position, the at least one armature forms a second port-magnetic-circuit with the casing and the second front section, said port-magnetic-circuit surrounding at least the second coil, while the working air gap with the first front section are opened to a maximum degree, wherein at least a first and a second permanent magnet are provided, wherein the first and the second coil are arranged in the axial direction between the first and the second permanent magnet, wherein the first permanent magnet applies a magnetic voltage to the casing and the first front section and the second permanent magnet applies a magnetic voltage to the casing and the second front section.

14. A control system for a locking element according to claim 1.

15. A joint orthosis or joint prosthesis, comprising a first element and a second element that are connected to one another via a swivel joint such that they can be swivelled and with an electromagnetic locking element according to claim 1 for locking the swivel joint in an extended position or locking the joint orthosis or joint prosthesis.

16. An electromagnetic locking element for locking an orthosis joint or prosthesis joint, comprising:
a bistable solenoid with at least one coil and at least one permanent magnet;
a pin movable between retracted and extended positions by operation of the solenoid to lock the joint;
at least one electrical energy store;
an electrical control system configured to discharge the at least one energy store via the at least one coil of the solenoid to move the pin; and
a spring system with a first spring, which exerts a force on an armature towards a central stroke position when in a first stroke end position, and a second spring, which exerts a force on the armature towards the central stroke position when in a second stroke end position, wherein the armature is held, permanently magnetized, against the spring force in both stroke end positions when no current is present.

17. The locking element according to claim 16, wherein the bistable solenoid has two end positions.

18. The locking element according to claim 17, wherein amounts of potential energy stored in the locking element in the two end positions, excluding the electrical energy and when no current is present, do not differ from one another by more than 50% of a greater of the stored potential energies.

19. The locking element according to claim 16, wherein the bistable solenoid has an asymmetrical characteristic line or the magnetic holding force of the solenoid is highest in the first or second end position in which the pin of the locking element is extended, which is reached by way of at least one of a geometric characteristic line modifier and the magnetic holding force in one of the first and second end positions is between 20% and 80% of the magnetic holding force in the other first and second end position.

20. The locking element according to claim 16, wherein the locking element has a resting point at a position in which, when no current is present, the pin is partially extended, wherein at least one of the pin, at the resting point, is extended sufficiently to lock the joint, the resting point is achieved by way of an asymmetrical characteristic line, and the resting point is at an offset in relation to a center of a stroke path.

* * * * *